United States Patent [19]

Link et al.

[11] Patent Number: 4,944,762
[45] Date of Patent: Jul. 31, 1990

[54] JOINT ENDOPROSTHESIS

[75] Inventors: Helmut D. Link, Hamburg; Arnold Keller, Kayhude, both of Fed. Rep. of Germany

[73] Assignee: interplanta Arzt-und Krankenhausbedarf GmbH, Hamburg, Fed. Rep. of Germany

[21] Appl. No.: 907,122

[22] Filed: Sep. 11, 1986

[30] Foreign Application Priority Data

Jun. 30, 1981 [DE] Fed. Rep. of Germany ....... 3125657
May 3, 1982 [DE] Fed. Rep. of Germany ....... 3216533

[51] Int. Cl.$^5$ ............................................. A61F 2/32
[52] U.S. Cl. ......................................... 623/23; 623/18
[58] Field of Search .................... 623/20, 21, 22, 23

[56] References Cited

U.S. PATENT DOCUMENTS

| | | | |
|---|---|---|---|
| 3,228,393 | 1/1966 | Michele | 3/1.913 |
| 3,782,373 | 1/1974 | Smythe | 623/23 |
| 3,991,425 | 11/1976 | Martin et al. | 623/21 |
| 4,276,660 | 7/1981 | Laure | 3/1.91 |

FOREIGN PATENT DOCUMENTS

| | | | |
|---|---|---|---|
| 0011665 | 6/1980 | European Pat. Off. | 3/1.913 |
| 2621666 | 11/1977 | Fed. Rep. of Germany | 3/1.91 |
| 426096 | 6/1967 | Switzerland | 623/22 |
| 560042 | 3/1975 | Switzerland | 3/1.913 |

*Primary Examiner*—Richard J. Apley
*Assistant Examiner*—David J. Isabella
*Attorney, Agent, or Firm*—Townsend and Townsend

[57] ABSTRACT

The invention relates to a femoral hip-joint endoprosthesis having a shaft to be inserted into the medullary cavity (4) of the femur (1) and a support plate (7), which terminates the shaft proximally and the under surface (12) of which is provided for support on the resection surface (16) of the bone. The overall axis (6) of the resection surface is inclined. The prerequisites for the transfer of forces from the prosthesis to the bone are improved when the under surface (12) and the resection surface (16), which is prepared to be of the same shape, are formed so that the medial part of the under surface includes an angle with the axis of the femur which is, on average, larger than its lateral part. A cylindrical shape of the two surfaces with a cylindrical axis running from anterior to posterior, or a spherical shape, are particularly advantageous. Furthermore, it is advantageous to form the under surface as a surface of revolution about a rotation axis running transverse to the under surface. This permits very exact preparation of the resection surface with a cutter which is held in a predetermined position by a holding shaft which coincides with the shaft of the prosthesis and which is inserted in the medullary cavity of the bone.

3 Claims, 2 Drawing Sheets

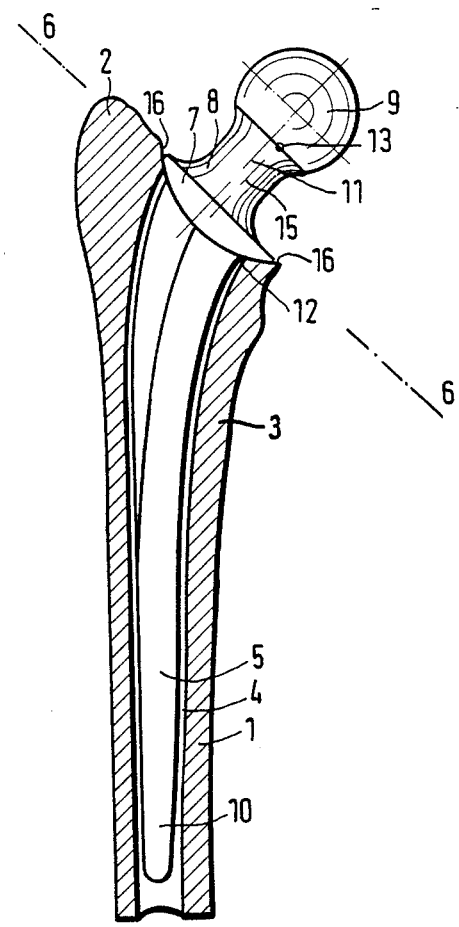
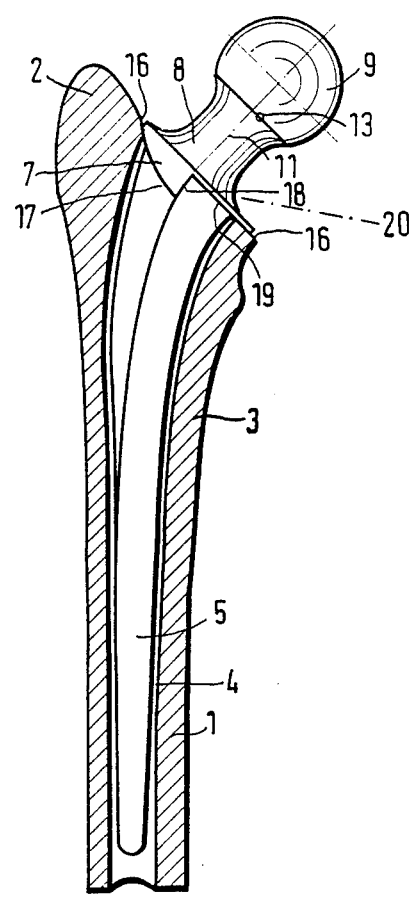

Fig. 3
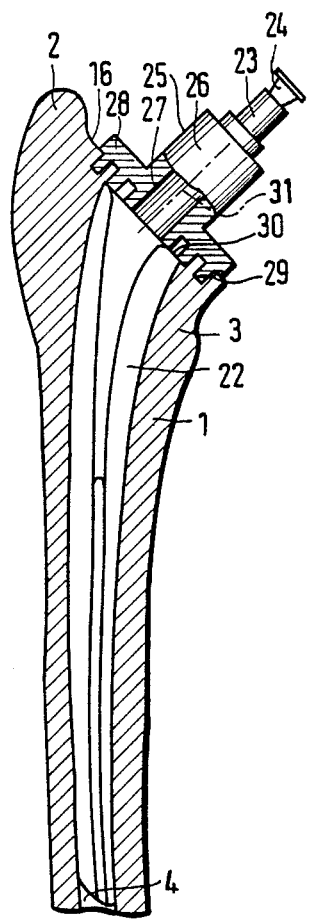
Fig. 4
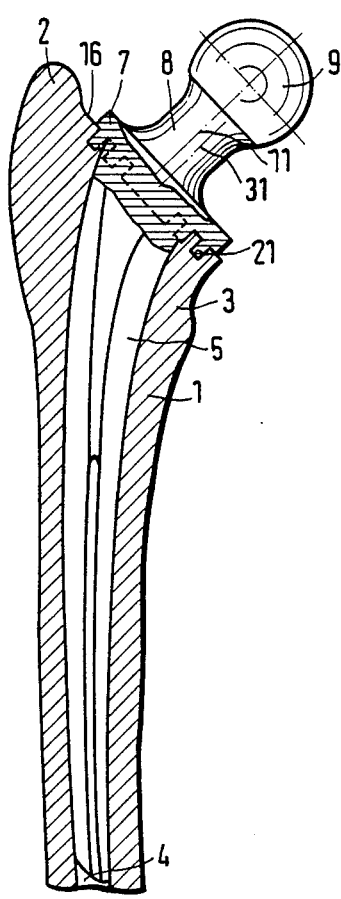
Fig. 6
Fig. 9
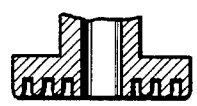
Fig. 7
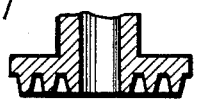
Fig. 5
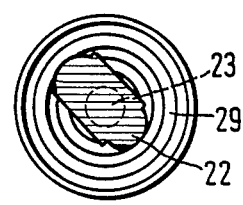
Fig. 8
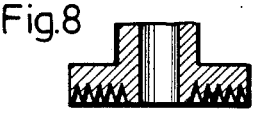
Fig. 10

JOINT ENDOPROSTHESIS

This is a continuation of application Ser. No. 391,818, filed Jun. 24, 1982, now abandoned.

DESCRIPTION

The invention relates to a femoral hip-joint endoprosthesis having a shaft to be inserted in the medullary cavity of the femur and a support plate, which terminates the shaft proximally, the under surface of which is provided for support on the resection surface of the bone, which runs at an angle to the longitudinal axis of the bone from the proximal side of the greater trochanter to the proximal side of the lesser trochanter, and which comprises sub-surfaces having different inclinations to the axis of the shaft in order to interact with sub-surfaces of the resection surface, which have been prepared with appropriate shapes.

The under surface of the support plate in most known hip-joint endoprostheses is flat. Since it is at an angle to the major direction of load, its capacity for force transfer is limited. Furthermore, because of the effect of the inclined plane, it has a tendency to bring about a movement of the prosthesis relative to the bone and directed medially. In order to prevent this, manufacturers have already provided the under surface of the support plate with corrugations or teeth, which are pressed into the surface of the bone on insertion of the prosthesis and are thus intended to produce an anchoring effect against relative lateral movements (German Offenlegungsschrift 2,839,093). However, in practice, this object can be achieved only to a limited extent, because it is very difficult to press the prosthesis against the resection surface during surgery hard enough for the teeth to penetrate the hard cortical substance sufficiently. It is also difficult to shape the resection surface exactly enough for the under surface of the support plate to lie exactly parallel to the resection surface when the prosthesis is positioned according to requirements so that all the teeth can be equally involved in the engagement.

A hip-joint endoprosthesis is known (German Offenlegungsschrift 2,931,750) in which the under surface of the support plate should have a lower angle of inclination than is otherwise customary. However, it seems very doubtful whether this proposal can be put into practice, because the direction of slope of the resection surface is not freely selectable, but is predetermined by the positions of the greater and lesser trochanters, proximally adjacent to which it must be led along so that, in general, an angle of inclination of about 45° is produced.

The invention makes the basic assumption that the mean course of the resection surface is predetermined by the positions of the greater and lesser trochanters and thus that its average inclination cannot be altered.

Thus the invention has the object of providing an endoprosthesis of the type mentioned in the introduction which makes possible both an improved and more reliable transfer of forces between the under surface of the support plate and the resection surface of the femur.

The object is achieved according to the invention in that the medial part of the under surface of the support plate includes, with the axis of the femur, a larger angle on average than its lateral part.

The steeper course of the under surface in the lateral region makes possible a correspondingly flatter course in the medial region so that more favourable conditions for the transfer of vertical forces from the prosthesis to the resection surface are present there. An important part of the invention is thus based on the concept of shaping the resection surface to correspond to the under surface so that the under surface interlocks securely with the resection surface, at least in those regions of the surface in which, due to their forming a lowre angle, the vertical forces are largely transferred. At the same time, the invention also ensures that the force transfer surfaces provided on the shaft are more effective, because the effect of the inclined plane, which additionally loaded these surfaces or decreased their load-carrying ability because of the relative movement of the prosthesis under loading directed medially, is decreased.

The axis of the femur, to which the inclination of the sub-surfaces in the under surface of the support plate is related, may even by clearly defined when the prosthesis has not yet been inserted. This is because there are particular instructions for use of each type of prosthesis from which the position of insertion in the bone and thus the bone axis is specifically derived. Even without this information, the longitudinal axis of the femur can be approximately taken to be that of the neck part of the prosthesis shaft. The neck part normally has, as does the natural neck of the femur, an angle of about 43° to 45° to the longitudinal axis of the femur. The prosthesis shaft generally projects on a distal end in the axis of the femur. The terms lateral and medial parts of the under surface are intended to indicate its principal surfaces, but their boundary does not necessarily coincide with the centre of the under surface. Nor is it requisite that each sub-surface itself has a constant inclination or can be regarded as a unit in respect of inclination. On the contrary, each subsurface itself can also be constructed in steps. Nor does the boundary between the two sub-surfaces need to be visually obvious, if, for example, a curved transition from one sub-surface into the other is envisaged.

A shaped which consists of steps which are each plane or consist of plane sub-surfaces is advantageous, because this may be prepared relatively accurately with the customary bone saw without great difficulty.

In addition, it can be provided according to the invention that the under surface of the support plate is a surface of revolution having a proximal turning axis. This characteristic makes possible the preparation of the resection surface as a surface of revolution with suitable cutting tools. Thus, the under surface of the support plate can, for example, be distinguished by a cylindrical shape having a turning axis running parallel to the under surface from anterior to posterior. A spherical shape can also be advantageous in respect of the ease of preparation and a secure and unambiguous positioning of the prosthesis. Simple shapes are preferred. Angular transitions from one sub-surface to the other are preferably provided in the medial or central region of the resection surface, in order to prevent deleterious fatigue strength reduction in the region of force transfer to the greater trochanter.

According to a particular characteristic of the invention, the under surface of the support plate is shaped as a surface of revolution, which deviates from the plane shape, having a turning axis transverse thereto, in particular, it having the shape of a spherical cap or a multiplicity of ring-shaped corrugations. With such a position of the surface of revolution and its turning axis, a particularly exact cutting of the resection surface using a surgical instrument can, in fact, be achieved, the instrument consisting of a rotatable cutter having a cutting shape corresponding to the under surface of the support plate of the prosthesis and having a cutter holder with a bearing device suitable for the cutter and a shaft which holds this and which corresponds to the shape of the shaft of the endoprosthesis. In this process, it should generally be provided that the bearing device has a turning axis which is fixed or fixable with respect to the axis of the shaft, although this is not absolutely necessary when the support plate is not connected with the prosthesis with a rigid axle, but, for example, with a movable ball joint.

It is particularly advantageous to use the prosthesis having a surface of revolution transverse to the under surface of the support plate and to use the relevant surgical instruments to cut the resection surface for femoral hip-joint endoprostheses. However, these concepts of the invention can also be used for other types of shaft prostheses.

The correspondence between the shafts of the prosthesis and the cutter holder should be as large as possible, so large in fact that the reliability of positioning of the cutter axis is sufficient. However, for ease of manipulation, the shaft of the cutter holder can generally be designed somewhat thinner than that of the prosthesis shaft. Its length can also be somewhat less. In the design of the details, the shaft of the cutter holder can also deviate, as long as this does not adversely affect the correspondence of the position in the medullary cavity of the bone.

The characteristic that the under surface of the support plate is a surface of revolution is not intended to state that its outer boundary must also be a surface of revolution. On the contrary, the under surface can project to different extents in different directions. For example, it can be provided that the support surface projects further medially than laterally. It is also unnecessary for the axis of revolution of the support surface to coincide with the axis of the prosthesis shaft or of the neck of the prosthesis.

The invention is illustrated in more detail in the following text, making reference to the drawing which depicts advantageous exemplary embodiments. This shows:

FIG. 1 a femur with prosthesis in place, the support plate of which is cylindrically shaped on the under surface, FIG. 2 an embodiment having an under surface which is shaped in steps, FIG. 3 a lateral-medial longitudinal section through a femur with a cutting insturment in place, FIG. 4 the arrangement according to FIG. 3 having a prosthesis in place instead of the cutting instrument, FIG. 5 a cross-section through the cutter holder seen parallel to the plane of cutting and to the cutter, and FIGS. 6 to 10 cross-sections through various shapes of cutter.

The stippled areas in FIGS. 1 to 4 show the cut surfaces of the bone 1 with the greater trochanter 2 and the lesser trochanter 3 and the medullary cavity 4, which has been prepared to receive the shaft of the prosthesis. The neck of the femur is resected along the plane, the main axis of which is indicated by the dot-and-dash line 6, which must be situated laterally high enough for the greater trochanter 2 to be retained, whilst medially it must be low enough for the neck part to have approximately the length shown, which is necessary in order to provide the femur with a sufficient range of swivel with respect to the acetabulum. The resection line 6 thus always makes an angle somewhat less than 45° with the longitudinal axis of the femur 1.

The prosthesis consists of the shaft 5, the support plate 7, the neck part 8 and the articular head 9. The shaft is inserted into the medullary cavity 4, with or without bone cement, and indicates the axis of the femur in its distal section 10. The axis 11 of the neck part 8 makes an angle of less than 45° to the axis of the femur.

In the exemplary embodiment according to FIG. 1, the under surface of the support plate 7 is formed by a cylindrical surface 12, the centre line of which passes through the plane of the drawing perpendicularly at 13. In its central region it is interrupted by the attachment of the shaft 5, whilst its outer boundary is the edge of the support plate 7, which is to be imagined as the surface of a regular cylinder about the axis 15. Instead of the circular boundary edge of this support plate 4, obviously a rectangular or oval boundary or another shape is also possible. The support plate 7 with its cylindrical under surface 12 is displaced slightly in a medial direction with respect to the central line 11 of the neck part 8 in order to accentuate the medial region of the under surface which is more important than the lateral part for transfer of force to the bone.

The resection surface 16 of the bone which is only approximately defined by the line 6 is shaped cylindrically in an identical manner to the under surface 12 of the support plate. The radius of the cylinder is chosen so that the under surface 12 of the prosthesis or the resection surface 16 make an angle with the longitudinal axis of the femur which is medially almost a right angle. By this means, in the region of the hard medial cortical substance, an excellent transfer of the vertical forces from the prosthesis to the femur is obtained. This also applies (even though to a smaller extent) to the other parts of the under surface 12 lying medially with respect to the middle line 15, since they make a smaller angle compared with line 6. On the other hand, the resection surface 16 makes a larger angle laterally from the middle line 15. However, this is of only slight relevance for the transfer of force.

Based on FIG. 1, the under surface 12 of the support plate 7 can also be imagined as spherically shaped having a centre of curvature 13. The advantages of this type of design substantially coincide with those of a cylindrical design, with the addition of a stabilisation of the prosthesis in the direction perpendicular to the plane of the drawing. In both cases, the area of the greater trochanter 2 remains unimpaired. Indentations, which would be disadvantageous in respect of rigidity, are also avoided.

When the under surface 12 and the resection surface 16 are designed cylindrically, these surfaces generate straight lines which run perpendicularly to the plane of the drawing and thus the surfaces can be prepared with great accuracy by cutting with a tool which is designed straight and perpendicular to the plane of the drawing or which is moved in this direction. It is also possible, instead of this, to carry out the cutting with a rotating tool, the rotation axis of which runs perpendicular to the plane of the drawing through the centre of curvature 13.

In the example in FIG. 2, the under surface of the support plate 7 and thus also the resection surface of the femur consist of a curved lateral surface part 17, which is relatively steep, of a step surface 18, which is approximately in the centre of the under surface and which runs in a plane which is transverse to the plane of the drawing and parallel to the axis 11 of the neck of the femur 8 and of a surface 19 which runs perpendicular thereto, the surface 17 being shaped cylindrically about the axis 13, which runs perpendicular to the plane of the drawing. The surfaces 18 and 19 form the medial part of the under surface, which includes a larger angle with the longitudinal axis of the bone compared to the lateral part 17. In fact, if the average axis of the two surfaces 18 and 19 is found, which is indicated by the dot-and-dash line 20, it is clear that this forms a comparatively large angle with the longitudinal axis of the bone. The step surface 18 takes up those components of force which act on the prosthesis in a medial direction relative to the bone because of the action of the surface portions 17 and 19 is inclined planes. Thus, overall, the surfaces 18 and 19 are exceptionally suitable for taking up vertical forces while preventing any displacement of the prosthesis in a medial direction relative to the bone.

Since all these surfaces generate straight lines which are parallel and perpendicular to the plane of the drawing, the resection surface 16 of the bone can also be easily and exactly shaped in this case.

It is unnecessary for the surface 18 to be as steep, that is to say to have such a small angle with the axis of the neck as is shown in the drawing. A less steep angle is frequently adequate, in which case the surface portion 19 can also be designed correspondingly flatter. A multiplicity of step surfaces 18 can be provided. The limit for their number, or for the fineness of the toothing which arises when the number of steps is relatively large, is where the smallness of the individual surfaces no longer leads to the expectation that the preparation of the resection surface of the bone will be sufficiently accurate. A corrugated shape is also possible instead of a step shape.

The prosthesis shown in FIG. 4 differs from the prostheses described previously in that the under surface 21 of the support plate 7 is designed such that the main extent of this surface is plane and perpendicular to the plane of the drawing. It has a multiplicity of ring-shaped ribs and grooves, the course of which is made clear in FIG. 5. The resection surface 16 of the bone 1 contains corresponding ribs and grooves which are formed to be complementary. In many cases, the exact correspondence of the shapes of the resection surface and the under surface of the support plate permits cement-free anchoring of the support plate (at least) to the bone.

Preparation of the resection surface 16 is carried out by the instrument shown in FIG. 3. This is located on a shaft 22 which corresponds exactly with the shaft of the prosthesis, so that there is sufficient certainty that the former occupies the same position in the bone as does the shaft of the prosthesis subsequently. A bearing journal 23 is rigidly attached to the shaft 22. The position of the former coincides with the rotation axis fo the support surface 21 of the neck support of the prosthesis. The bearing journal 23 has on its end a shaping 24, which permits a tool to grip for removing the cutter holder from the bone. The cutter 25 is placed on the bearing journal 23, the former consisting of a hub 26 having a bearing bore 27 fitting the journal 23 and a cutting plate 28, which carries cutting teeth 29 on its underside which provide the desired surface profile on rotation.

FIG. 3 illustrates the cutter 25 in the final position of the cutting procedure, in which it has advanced as far as the covering surface 30 of the shaft 22. Thus, this figure also illustrates the final shape of the resection surface corresponding to FIG. 4.

On comparison of FIGS. 3 and 4, it can be seen that the axis 31 of the cutter 25 and the under surface 21 are somewhat displaced in a medial direction relative to the axis 11 of the neck of the prosthesis.

FIGS. 6 to 10 illustrate various profiles which are practicable on the under surface 21 of the neck support within the scope of the invention.

The invention is principally suitable for those prostheses in which the shape of the shaft ensures a secure angular position in the medullary cavity and which, for this purpose, have the curvature characteristic of the medullary canal, not only in the lateral-medial plane, but also in the anterior-posterior plane.

The description of the support surface 21 of the support plate as being a surface of revolution does not exclude that additional surface portions are present which recede and which are not formed as surfaces of revolution, for example radial grooves, which fulfil the function of preventing turning relative to the bone after filling the bone tissue or cement.

We claim:

1. A joint endoprosthesis for use with an elongate bone having a bone axis, a hollow interior and a joint end, the joint end modified to expose the hollow interior and create a cylindrical prepared joint surface, the joint surface surrounding one end of the hollow interior and having a resection line at an angle to the elongate bone axis, the joint endoprosthesis comprising:
    an elongate shaft defined by a longitudinal axis and having first and second ends, said first end configured to be inserted into the hollow interior of said bone and said second end to be adjacent to the prepared joint surface;
    said second end having attached thereto a support plate having an upper surface and a lower surface, said lower surface defining a cylindrical convex surface corresponding to a concave shape of the prepared joint surface;
    a combination neck and joint head extending from said upper surface of the support plate wherein said combination neck and joint head defines a central axis; and
    said cylindrical surface having an axis of rotation which is spaced eccentrically from said central axis.

2. The joint endoprosthesis of claim 1 wherein the central axis is at an acute angle to the longitudinal axis.

3. The joint endoprosthesis of claim 2, wherein said central axis is at an angle of about 45 degrees to said longitudinal axis.

* * * * *